(12) United States Patent
Jackson et al.

(10) Patent No.: US 6,830,554 B2
(45) Date of Patent: Dec. 14, 2004

(54) TAMPON APPLICATOR WITH TAPED FINGER GRIP

(75) Inventors: Dane R. Jackson, Bloomingdale, NJ (US); Suzanne A. Downs, Hohokus, NJ (US); Robert C. Norquest, Dover, DE (US)

(73) Assignee: Playtex Products, Inc., Westport, CT (US)

( * ) Notice: Subject to any disclaimer, the term of this patent is extended or adjusted under 35 U.S.C. 154(b) by 0 days.

(21) Appl. No.: 10/134,571

(22) Filed: Apr. 29, 2002

(65) Prior Publication Data

US 2002/0165480 A1 Nov. 7, 2002

Related U.S. Application Data

(62) Division of application No. 09/132,783, filed on Aug. 12, 1998, now Pat. No. 6,416,488.

(51) Int. Cl.⁷ .................................................. A61F 13/20
(52) U.S. Cl. ........................................... 604/11; 604/59
(58) Field of Search ............................... 604/11–18, 57, 604/59–60

(56) References Cited

U.S. PATENT DOCUMENTS

| | | |
|---|---|---|
| 2,489,502 A | 11/1949 | Ruth |
| 2,491,017 A | 12/1949 | Robinson |
| 2,587,717 A | 3/1952 | Fourness |
| 2,922,423 A | 1/1960 | Rickard et al. |
| 3,148,680 A | 9/1964 | Roberts et al. |
| 3,347,234 A | 10/1967 | Voss |
| 3,351,060 A | 11/1967 | De Woskin |
| 3,390,671 A | 7/1968 | Hildebrand |
| 3,543,754 A | 12/1970 | Jones, Sr. |
| 3,572,339 A * | 3/1971 | Voss et al. ................. 604/15 |
| 3,575,169 A | 4/1971 | Voss et al. |
| 3,581,744 A | 6/1971 | Voss et al. |
| 3,628,533 A | 12/1971 | Loyer |
| 3,645,263 A | 2/1972 | Bates |
| 3,895,634 A | 7/1975 | Berger et al. |
| 4,271,835 A | 6/1981 | Conn et al. |
| 4,286,595 A | 9/1981 | Ring |
| 4,351,338 A | 9/1982 | Langlois et al. |
| 4,412,833 A | 11/1983 | Wiegner et al. |
| 4,573,963 A | 3/1986 | Sheldon |
| 4,573,964 A | 3/1986 | Huffman |
| 4,622,030 A | 11/1986 | Sheldon et al. |
| 4,891,042 A | 1/1990 | Melvin et al. |
| 5,273,521 A | 12/1993 | Peiler et al. |
| 5,290,501 A | 3/1994 | Klesius |
| 5,330,421 A | 7/1994 | Tarr et al. |
| 5,395,308 A | 3/1995 | Fox et al. |
| 5,491,015 A * | 2/1996 | Reeves et al. ............. 428/167 |

\* cited by examiner

*Primary Examiner*—John J. Calvert
*Assistant Examiner*—Michele Kidwell
(74) *Attorney, Agent, or Firm*—Ohlandt, Greeley, Ruggiero & Perle, llp

(57) ABSTRACT

The present invention is an applicator barrel with a taped finger grip. The applicator barrel includes a barrel body having an outer surface. A three-dimensional tape is connected to a portion of the outer surface and includes a first surface and a second surface opposite said first surface. The first surface has at least one integrally formed gripping structure extending outwardly from the first surface to provide a gripping surface, and the second surface is adhesive to connect the tape to the barrel.

33 Claims, 7 Drawing Sheets

TAMPON APPLICATOR WITH TAPED FINGER GRIP

This is a division, of application Ser. No. 09/132,783, filed Aug. 12, 1998 now U.S. Pat. No. 6,416,488.

BACKGROUND OF THE INVENTION

1. Field of the Invention

The present invention is related to a tampon applicator and, more particularly, to a tampon applicator with a taped finger grip. The taped finger grip has a three-dimensional shape.

2. Discussion of the Prior Art

Tampon applicators are used to inject an absorbent or hygienic material, known as a tampon pledget, into a vaginal cavity. The use of such applicators requires that a user grip the applicator and guide it easily into the vaginal cavity. This is particularly important since a portion or all of the applicator is out of a direct line of vision of the user during insertion. Accordingly, applicators that are difficult to grip and control can hinder proper and rapid delivery of the pledget and, moreover, may result in discomfort to the user during delivery of the pledget.

Another problem associated with a difficult to grip applicator is that the user often applies excessive gripping force on the body of the applicator to compensate for the lack of gripability. This excessive force may partially deform and damage the body of the applicator, thereby distorting the cross-section of the applicator and obstructing the normal pathway of the plunger therefrom. As a result, the user may be required to apply a significant amount of force to eject the pledget from the applicator.

One approach to provide the user with improved gripability is to form a finger grip that is unitary to the tampon applicator. The finger grip can be formed by embossing either an outside surface or inside surface of an already formed applicator. The embossed portion of the applicator typically takes the form of a series of raised circumferential rings or a series of discrete raised dots aligned in several circumferential rows. Examples of such finger grips can be found in U.S. Pat. No. 5,395,308 to Fox et al., U.S. Pat. No. 5,290,501 to Klesius, U.S. Pat. No. 4,573,964 to Huffman; U.S. Pat. No. 4,573,963 to Sheldon; U.S. Pat. No. 4,891,042 to Melvin et al.; U.S. Pat. No. 4,412,833 to Wiegner et al.; U.S. Pat. No. 3,895,634 to Berger; U.S. Pat. No. 3,628,533 to Leyer; U.S. Pat. No. 2,587,717 to Fourness; U.S. Pat. No. 2,489,502 to Ruth and U.S. Pat. No. 2,922,423 Rickard et al.

However, the use of such embossing techniques on the applicator has several drawbacks. On a film coated applicator, embossing a gripping surface on the applicator does not supply an adequate grip especially if the user has wet hands. On a non-film coated applicator, embossing a gripping surface on the applicator can easily punch through the cardboard, thereby resulting in a rough finger grip that may be uncomfortable to the user.

Another approach to the gripping problem is found in U.S. Pat. No. 3,575,169 to Voss et al., which generally discloses the use of separate raised elements that are applied to an outer tube of a tampon applicator to provide a finger grip. The elements can be formed of plastic, rubber, ceramic, paper or cardboard, and can either be affixed to the outer tube by interference fit or by bonding. For instance, a ring of glue can be applied to the outer tube at the finger grip position, and abrasive particles can be ducted onto the glue, before drying.

U.S. Pat. No. 3,347,234 to Voss discloses a tampon applicator with an outer tube that is strengthened to resist deformation from gripping pressure. Tampon applicator includes a strengthening ring which is applied to the outer tube at the finger grip. The ring can be formed of paperboard, emery board, paper, plastic or similar material, and can either be in the form of a strip, or as a continuous ring. The strip or ring can be bonded to the outer tube by adhesive.

However, both U.S. Pat. Nos. 3,575,169 and 3,347,234 disclose finger grips that require numerous steps to assemble onto the tampon applicator, thereby increasing the complexity and manufacturing cost of the tampon applicator. That is, an adhesive is applied to either each separate gripping element or the outer surface of the tampon applicator. Each separate gripping element is then affixed to the outer surface of the tampon at the finger grip area. Moreover, the cardboard and paper grips may not maintain their shape. The emery board and plastic grips are cumbersome and aesthetically displeasing.

Thus, there is a need to provide a finger grip that provides increased gripping than those in the prior art, and is simple and cost effective to manufacture. There is also a need to provide a finger grip that can be assembled onto a tampon applicator with ease.

SUMMARY OF THE INVENTION

Accordingly, it is an object of the present invention to provide a finger grip that allows tampon applicators to be manufactured with a greater selection of coatings on the non-grip area so as to facilitate insertion ease and comfort without negatively impacting the ability to grasp the applicator during the use.

It is another object of the present invention to provide such a finger grip which is simple and low in cost to manufacture.

It is a further object of the present invention to provide such a finger grip that can be connected to the tampon applicator before or after assembly of the applicator components.

In view of the foregoing, the present invention provides a tampon applicator barrel with a three-dimensional finger grip tape. The tampon applicator barrel includes a barrel and a three-dimensional finger grip tape connectable to a portion of the outer surface of the barrel. The tape is preferably positioned proximal to the rear of the barrel. The tape includes a first surface having at least one integrally formed raised structure to provide a textured surface, and a second surface opposite the first surface. The first surface of the tape provides a textured surface with improved gripability. The second surface is adhesive to connect the tape to the barrel. This may be accomplished by applying an external adhesive onto the second surface, or heating the second surface to a suitable temperature so that the second surface becomes adhesive.

In addition thereto, either in conjunction with the raised areas or without, the tape may be tacky or slightly rough, or have a higher coefficient of friction than the coating on the applicator's non-grip areas. The taped finger grip would allow selection of coatings on the non-grip area which facilitate insertion ease and comfort without negatively impacting the ability to grasp the applicator.

The invention uses a tape that is circumferentially applied as a band to the finger grip area anytime after the applicator tube is formed. In the case where flat cardboard or paperboard blanks are convolutely formed into applicators, the taped grip could be applied prior to forming.

BRIEF DESCRIPTION OF THE DRAWINGS

The foregoing and other objects and advantages of the present invention will be more apparent from the following detailed explanation of the preferred embodiments in connection with the accompany drawings in which.

DETAILED DESCRIPTION OF THE PREFERRED EMBODIMENTS

Figure 1:
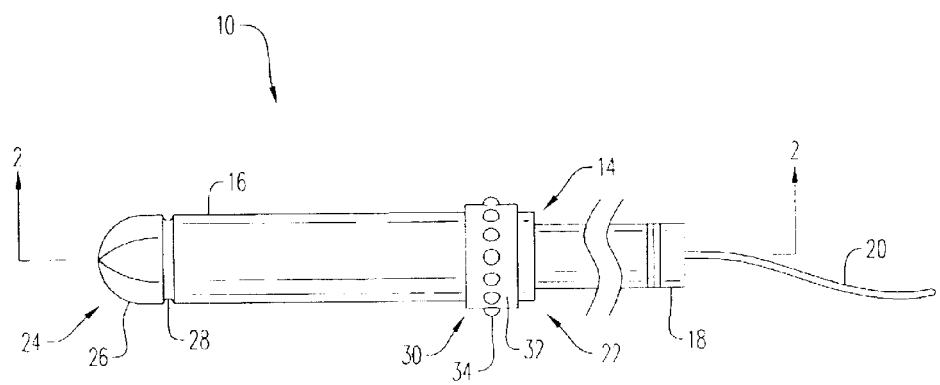
FIG. 1 illustrates a tampon assembly with a tape finger grip in accordance with the present invention.
Figure 2:
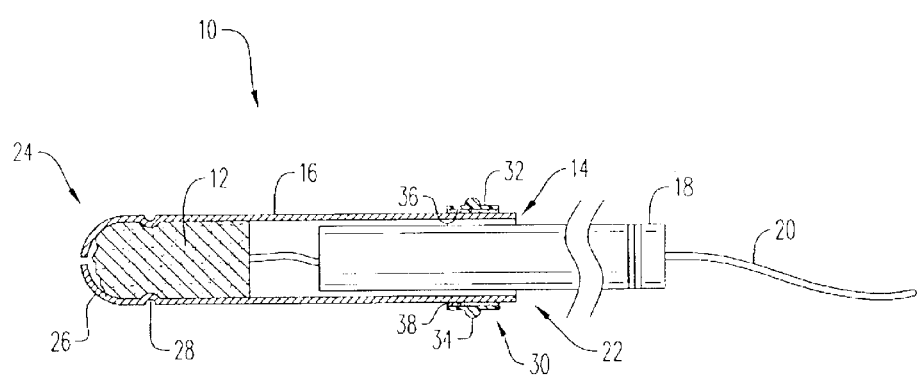
FIG. 2 illustrates a side cross-section view of the tampon assembly of FIG. 1.

Referring to the figures and, in particular, FIGS. 1 and 2, there is shown a first embodiment of a tampon assembly generally represented by reference numeral 10. Tampon assembly 10 includes a pledget 12 and an applicator 14. Applicator 14 includes a barrel 16 with an expulsion end and a distal end 22 for retaining pledget 12 therein and preferably includes a plunger 18. Plunger 18 is adapted to slidingly engage distal end 22 of barrel 16 and to contact pledget 12 to expel the pledget through expulsion end 24. Pledget 12 is retained in barrel 16, and has connected thereto a pledget withdrawal cord 20 that extends through plunger 18 and out of a distal end 22 of applicator 14. Expulsion end 24 of barrel 16 preferably includes a plurality of petals 26 and a preformed hinge or groove 28 disposed circumferentially on or at a base of the petals. Preferably, the plurality of petals 26 are collectively shaped to form a dome or any shape in general which facilitates insertion.

Tampon assembly 10 further includes a three-dimensional finger grip tape 30 connectable to an outer surface portion of barrel 16, preferably proximal distal end 22 of barrel 16. Finger grip tape 30 includes a first surface 32 and a second surface 36 opposite the first surface. First surface 32 includes at least one raised structure 34 extending outwardly from first surface 32 to provide a gripping or textured surface. Raised structure 34 can be formed either by embossing finger grip tape 30 after formation thereof or molding the finger grip tape during the formation thereof. Second surface 36 has provided thereon an adhesive layer 38. That is, second surface 36 has a pre-applied adhesive layer 38 which provides a self-adhesive surface for connecting taped finger grip 30 onto an outer surface of barrel 16.

It has been discovered that the use of finger grip tape 30 provides several advantages over known tampon gripping surfaces. One advantage is that finger grip tape 30 provides a simple and low cost method for forming a finger gripping surface on tampon applicators. Finger grip tape 30 can be fabricated with any material that can be embossed, molded or the like to provide at least one raised structure on the first surface 32. The self-adhesive second surface 36 with a pre-applied adhesive layer also allows finger grip tape 30 to be easily connected to an outer exterior portion of barrel 16, without numerous, complex, time consuming and cost prohibitive steps.

In addition, the use of finger grip tape 30 provides for increased design and manufacturing flexibility. In particular, finger grip tape 30 can be connected to a paper-based barrel 16, such as cardboard or paper laminate, prior to formation of the barrel. For example, finger grip tape 30 can be connected to a flat cardboard or paper laminate blank which is later convolutely formed into barrel 16. A more detailed description of such a method is provided below. Finger grip tape 30 can also be connected to barrel 16 anytime after formation thereof, such as onto a formed barrel of a tampon applicator.

Finger grip tape 30 also allows tampon applicators, particularly paper-based applicators, to be manufactured with a greater selection of film or liquid coatings on the non-grip areas to facilitate insertion ease and comfort, without negatively impacting the ability to grasp the applicator. Such coatings for applicators are typically chosen based on various factors, including gripability, particularly when the gripping surface is formed as part of the applicator. However, the non-unitary characteristic of finger grip tape 30 eliminates the need for selecting coatings on the basis of gripability. Accordingly, barrel 16 may employ various type of liquid or film coatings with disregard to the gripability issue (i.e., preferably a slicker coating), so long as finger grip tape 30 can be connected to the coated exterior surface of the barrel.

It is preferred that finger grip tape 30 has a three-dimensional construction with an appropriate thickness and at least one raised structure 34 extending from first surface 32. Raised structure 34 preferably extends a distance approximately 0.003 inch or greater from a base of first surface 32.

It is also preferred that finger grip tape 30 includes a plurality of raised structures 34 to provide increased gripping texture. Finger grip tape 30 preferably has a width between approximately one-half inch to approximately one inch, and a length approximately equal to a circumference of barrel 16. As shown in FIGS. 1 and 2, finger grip tape 30 can thus be circumferentially applied as a band to the finger grip area of barrel 16.

It is also preferred that the coefficient of friction of finger grip tape 30, particularly of first surface 32, is greater than the coefficient of friction of an exterior surface of barrel 16. That is, first surface 32 of finger grip tape 30 provides a more gripable surface than an outer surface of barrel 16.

As briefly mentioned above, finger grip tape 30 can be formed of any material that can readily be made with outwardly extending structures, such as polypropylene. For instance, polypropylene film as well as other suitable films can be heat embossed to form outwardly extending raised structures on the gripping surface (i.e., first surface 32). Such films can also be heat debossed to form inwardly extending raised structures on the gripping surface. The adhesive used to connect tape 30 to applicator 14 may be pre-applied to the tape, or may be applied to the applicator or tape at the time of joining. Finger grip tape 30 may either be supplied in continuous lengths and cut to a desired size at the time of application or may be supplied precut as an adhesive backed label on a release liner which can be discarded after use.

Through experimentation, it has been discovered that finger grip tape 30 can be a tape manufactured by Minnesota Mining and Manufacturing Company, under the trade name STEM WEBB™. For example, STEM WEB™ No. XMO-5-064 can be applied to super absorbency cardboard applicators to form a 0.75 inch wide finger grip 30 at the plunger end of applicator barrel 16. This particular tape has an average raised structure height of 0.005 inch and raised structure density of approximately 2300 per square inch. It is preferred that the tape has a raised structure density of approximately 900 to 2500 per square inch.

The typical performance characteristics and physical properties of STEM WEB® is provided below:

TYPICAL PERFORMANCE CHARACTERISTICS:

| | | |
|---|---|---|
| 180° PEEL ADHESION | Stem side to Cotton | 170–200 gm/25 mm |
| | Stem side to nylon | 170–200 gm/25 mm |
| | Attachment side to Poly | 1000–1600 gm/25 mm |
| | Attachment side to non-woven | Exceeds internal strength of non-woven |
| Shear hang time | Stem side to cotton | 10,000 min/25 mm | dome-like shape extending from first surface 32. Gripping structures 34 are preferably arranged in a plurality of rows and columns.

Figure 5:
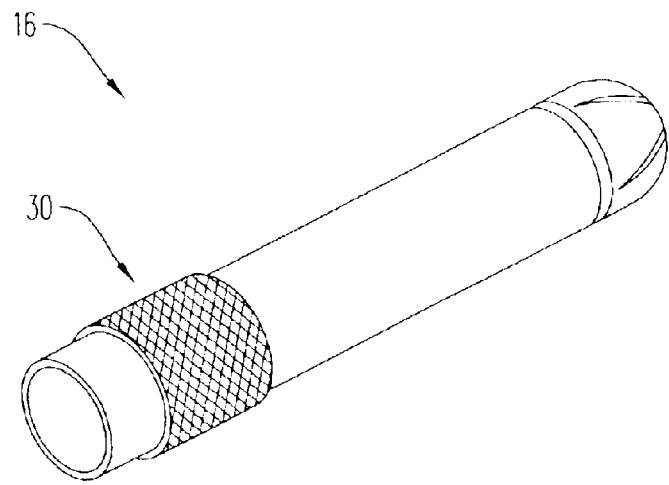
FIG. 5 illustrates a second embodiment of a textured surface of the tape finger grip arranged on the tampon applicator of the present invention.
Figure 6:
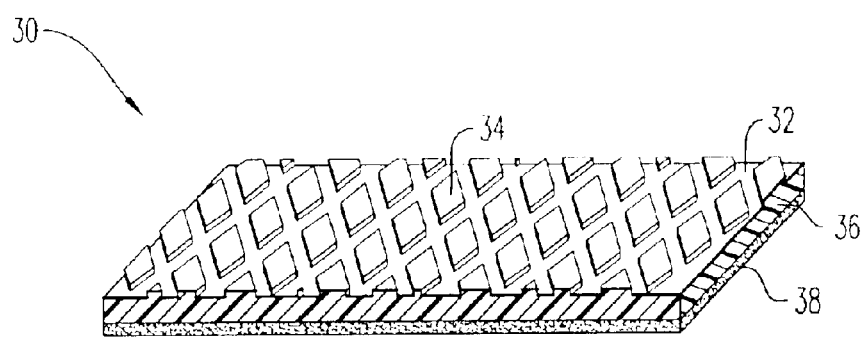
FIG. 6 is an enlarged view of the textured surface of the tape finger grip of FIG. 5.
Figure 7:
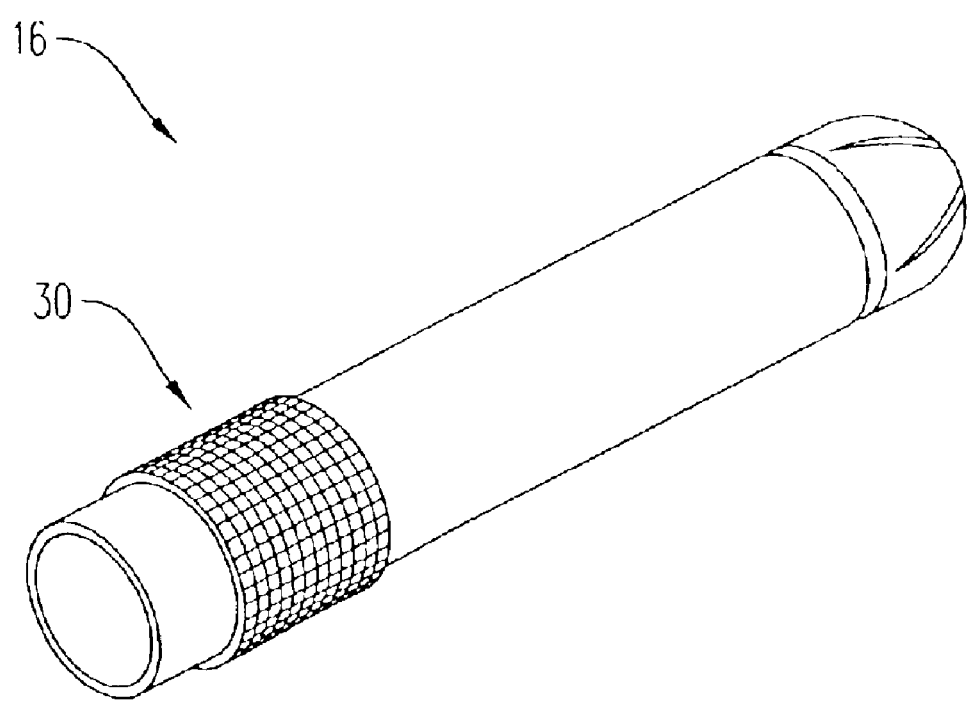
FIG. 7 is a third embodiment of the textured surface of the tape finger grip on the tape applicator of the present invention.

Referring to FIGS. 5 through 7, gripping structures 34 may also be arranged in a diamond pattern (FIGS. 5 and 6), a box pattern (FIG. 7) or a combination thereof, i.e., a diamond and box pattern. The above patterns may be formed on finger grip tape 30 by embossing, molding, cutting or any equivalent technique.

Figure 8:
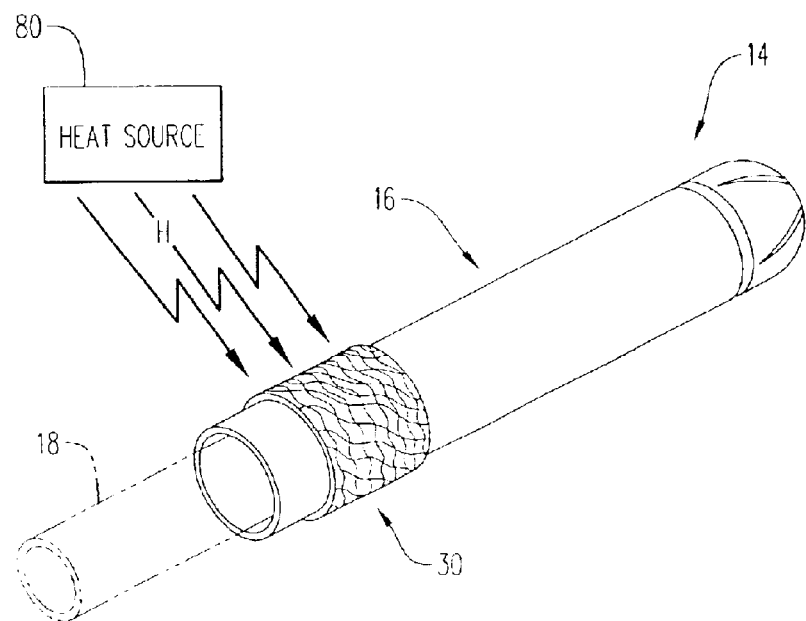
FIGS. 8 and 9 illustrate an alternative embodiment of a heat-activated taped finger grip that is heat bonded to a tampon applicator or component thereof in accordance with the present invention.
Figure 9:
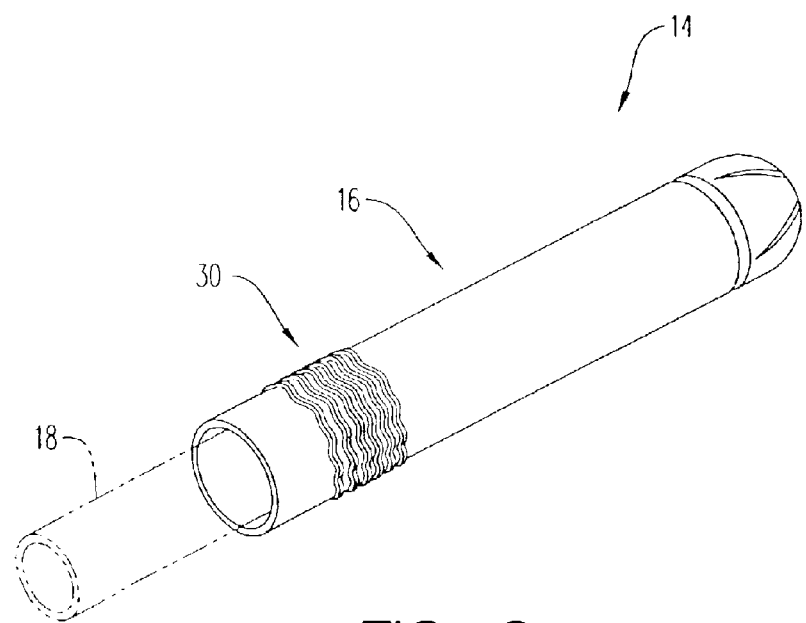

Referring to FIGS. 8 and 9, there is provided another embodiment of finger grip tape 30. In this embodiment, finger grip tape 30 is a heat-activated tape that can be heated to a suitable temperature to become adhesive. Finger grip tape 30 can thus be bonded to an outer surface of barrel 16 to form a finger grip without the use of an external adhesive.

Finger grip tape 30 can be made of any material that is capable of being heated to a suitable elevated temperature so as to become adhesive. The heated finger grip tape 30 that is in contact with barrel 16 thus bonds with the applicator or the components thereof to provide a rough, textured finger gripping surface. It is preferred that finger grip tape 30 can be made of a heat sensitive nonwoven material that is constructed using a low melting point polymer. Examples of such polymers may include copolyester, copolyamide, polyurethane or polyolefin. Finger grip tape 30 can be a nonwoven tape manufactured by Bostik (Middleton, Mass.), under its Web Adhesive and Sharnet® product lines (as described in the tables below).

WEB ADHESIVES

| PRODUCT | POLYMER TYPE | B & R M.P. (° C.) | DSC M.P. (° C.) | THERMAL VISCOSITY (cps) | MINIMUM BONDLINE TEMPERATURE (° C.) |
|---|---|---|---|---|---|
| PE 65 | Copolyester | 75 | 65 | 100,000 @ 180° C. | 70 |
| PE 75 | Copolyester | 90 | 82 | 140,000 @ 180° C. | 85 |
| PE 85 | Copolyester | 100 | 90 | 140,000 @ 180° C. | 93 |
| PE 103 | Copolyester | 115 | 103 | 140,000 @ 180° C. | 105 |
| PE 105 | Copolyester | 115 | 105 | 140,000 @ 215° C. | 115 |
| PE 120 | Copolyester | 131 | 120 | 125,000 @ 215° C. | 132 |
| PE 165 | Copolyester | 175 | 165 | 140,000 @ 215° C. | 180 |
| PA 115 | Copolyamide | 125 | N/A | 400,000 @ 180° C. | 121 |
| PA 145 | Copolyamide | 151 | N/A | 250,000 @ 180° C. | 143 |
| PO 90 | Polyolefin | 105 | N/A | 275,000 @ 180° C. | 88 |
| PO 104 | Polyolefin | 110 | N/A | 150,000 @ 180° C. | 115 |

-continued

| | | |
|---|---|---|
| | Attachment side to poly | >10,000 min/25 mm |

PHYSICAL PROPERTIES

| | | |
|---|---|---|
| Tensile at yield | Machine direction | 3400 gms/25 mm |
| | Cross direction | 2800 gms/25 mm |
| Elongation at break | Machine direction | >500% |
| | Cross direction | >500% |

Figure 3:
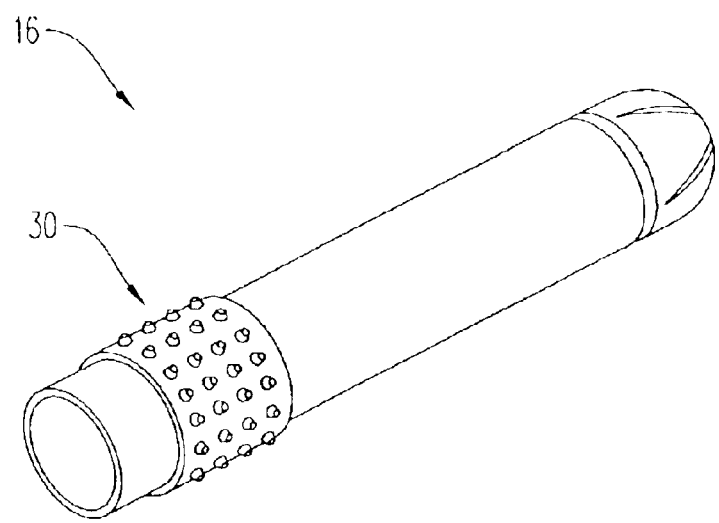
FIG. 3 illustrates a first embodiment of a textured surface of the tape finger grip arranged on the tampon applicator of the present invention.
Figure 4:
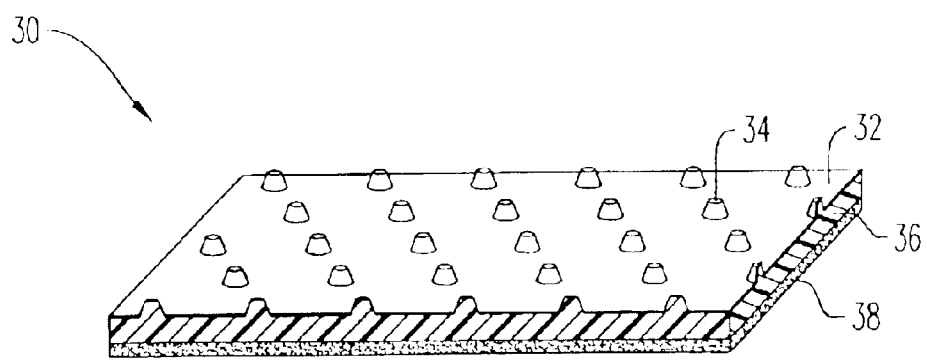
FIG. 4 is an enlarged view of the textured surface of the tape finger grip of FIG. 3.

Although gripping structures 34 can be formed or arranged in any pattern, or randomly, on finger grip tape 30, there is described below various preferred patterns. As shown in FIGS. 3 and 4, finger grip tape 30 may include gripping structures 34 having an approximately cone-like or

SHARENET ® Adhesive Webs

| PRODUCT | POLYMER TYPE | MINIMUM BONDLINE TEMPERATURE (° C.) | PROCESSING TEMPERATURE RANGE (° C.) | THERMAL RESISTANCE |
|---|---|---|---|---|
| SH 151 | Polyurethane | 125 | 150–190 | 120 |
| SH 191 | Polyurethane | 115 | 130–180 | 120 |
| SH 240 | Copolyamide | 90 | 120–160 | 110 |
| SH 2410 | Copolyamide | 95 | 135–200 | 120 |
| SH 2413 | Copolyamide | 90 | 120–160 | 110 |
| SH 3170 | Polyolefin | 140 | 170–200 | 130 |
| SH 4275 | Copolyester | 100 | 130–170 | 110 |

FIG. 8 illustrates an alternative embodiment of a tampon assembly 10 with a taped finger grip in accordance with the present invention. In this embodiment, finger grip tape 30 can be adhered or bonded to an applicator blank and/or barrel by heating a nonwoven material above its polymer softening point, through the use of a heat source 80, such as a hot air supply. The amount of heat (H) applied should be of a suitable level to adhere or bond the nonwoven material (e.g., a second surface in contact with the applicator) to applicator 14 or components thereof without significantly destroying the fiber texture of the nonwoven material. The resulting fiber surface of the bonded nonwoven material, particularly a first surface of the material, provides a rough, textured, gripping surface on barrel 16, as shown in FIG. 9. Heat-activated finger grip tape 30 can be fabricated with any material that can be heat bonded onto the applicator to provide a rough, textured, gripping surface.

It has been discovered that the use of a heat-activated finger grip tape 30 provides several advantages over known tampon gripping surfaces. One advantage is that the heat-activated finger grip tape provides a simple and low cost method for forming a finger gripping surface on tampon applicators. In particular, the use of a heat-activated finger grip tape eliminates the need for the use of an external adhesive layer as well as additional steps involved in applying and connecting the tape through the use of the external adhesive. Thus, the finger grip tape can be bonded to an outer exterior portion of barrel 16, without numerous, complex, time consuming and cost prohibitive steps.

Another advantage is that the heat-activated finger grip tape 30 also provides a stronger bond between the finger grip tape and the applicator, than would be provided by an external adhesive. Still another advantage is that some nonwoven materials may shrink slightly when subjected to heat. Such materials provide an additional benefit since the shrinkage results in improved contact between the nonwoven material and the applicator or components thereof and, thus, a stronger bond.

In addition, the use of a heat-activated finger grip tape provides for increased design and manufacturing flexibility. Finger grip tape 30 can be heated to an appropriate temperature so that the tape becomes adhesive and bonds with a paper-based barrel 16, such as cardboard or paper laminate prior to formation of the barrel. For example, finger grip tape 30 can be heat bonded to a flat cardboard or paper laminate blank which is later convolutely formed into barrel 16 of applicator 14. Heat-activated finger grip tape 30 can also be attached to barrel 16 anytime after formation thereof, such as onto a formed barrel or a formed barrel of an assembled applicator.

The heat-activated finger grip tape 30 also allows tampon applicators, particularly paper-based applicators, to be manufactured with a greater selection of film or liquid coatings on the non-grip areas to facilitate insertion ease and comfort, without negatively impacting the finger grip area. Presently, such coatings for applicators are typically chosen based on various factors, including gripability, particularly when the gripping surface is formed as part of the applicator. However, the non-unitary characteristic of finger grip tape 30 eliminates the need for selecting coatings on the basis of gripability. Accordingly, barrel 16 may employ various type of liquid or film coatings with disregard to the gripability issue (i.e., preferably a slicker coating), so long as finger grip tape 30 can be connected to the coated exterior surface of the barrel.

Figure 10:
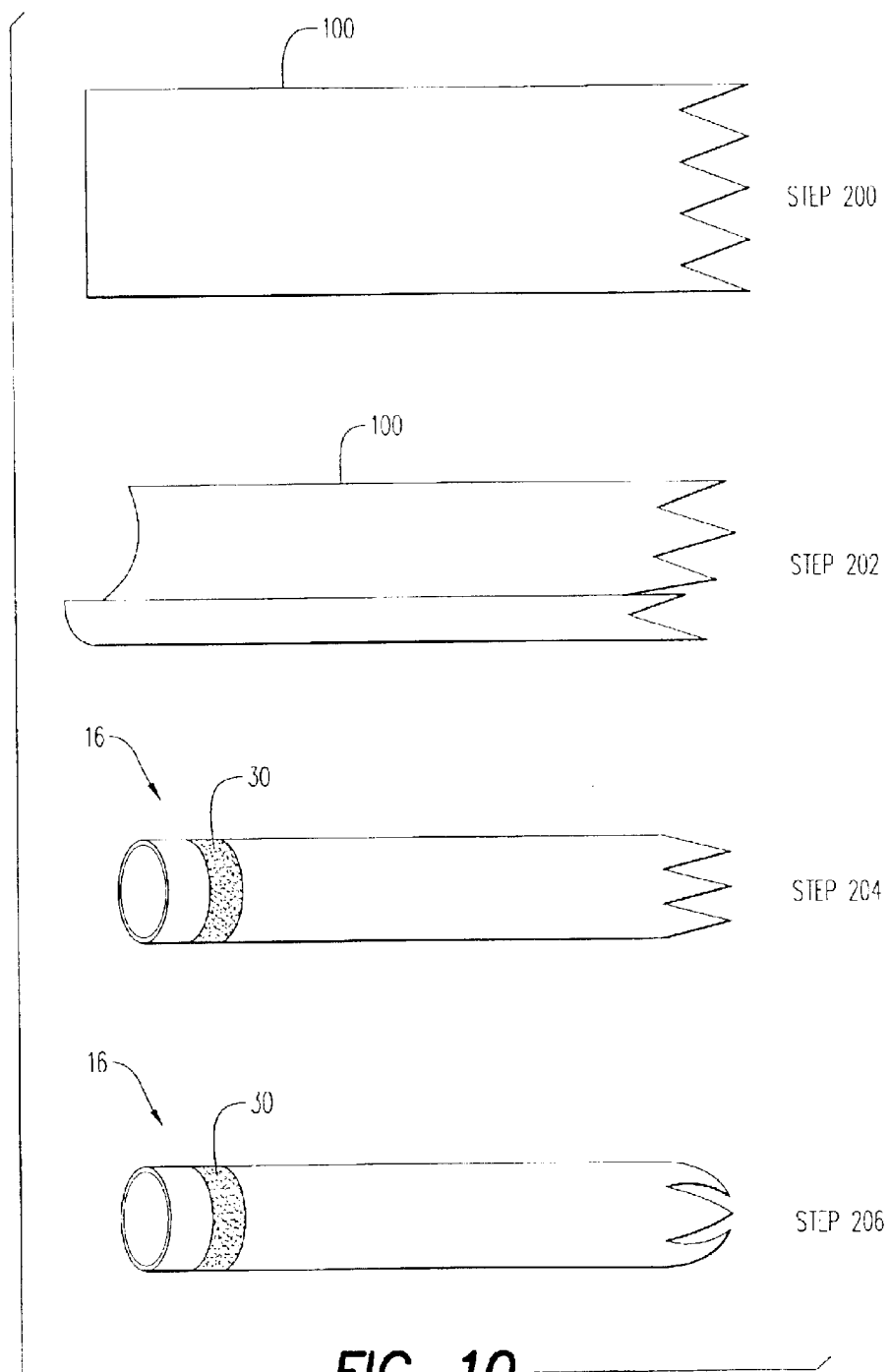
FIG. 10 illustrates a method of forming a tampon applicator barrel with a taped finger grip.

FIG. 10 illustrates the steps of forming a paper-based barrel 16 with a finger grip. Initially, a paper-based material blank 100, preferably a laminate paper board or a pre-coated paper board, is cut to a suitable size and shape (Step 200). Blank 100 is then convolutely wound to form barrel 16 (Steps 202). Finger grip tape 30 of the present invention is then connected or applied to a portion of barrel 16 (Step 204). Finger grip tape 30 may be connected to an outer surface portion of barrel 16 with an external adhesive which is pre-applied to the finger grip tape or may be applied to the barrel or the finger grip tape at the time of joining. Alternatively, finger grip tape 30 may be applied to an outer surface portion of barrel 16 and heated to a suitable temperature so that the tape, e.g., a second surface of the tape in contact with the barrel, bonds to the outer surface portion of the barrel. One cut end of barrel 16 can be formed into an insertion tip, preferably having a dome-shape (Step 206). The formed barrel 16 with finger grip tape 30 is then ready for assembly to form a tampon applicator and, subsequently, a tampon assembly.

Figure 11:
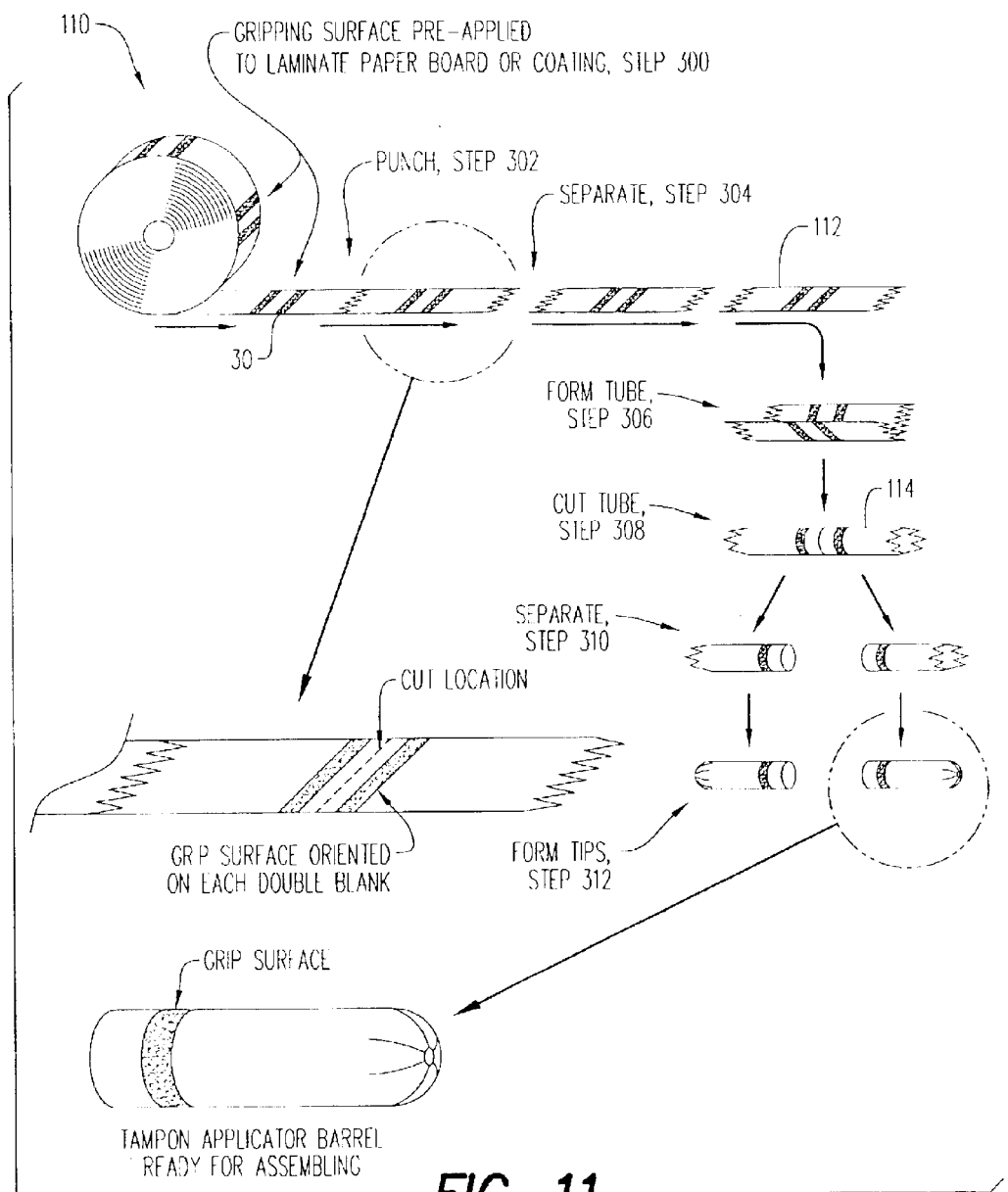
FIG. 11 illustrates another method of forming a tampon applicator barrel with a taped finger grip.

As shown in FIG. 11, there is provided an improved method for forming a tampon applicator barrel 16 to improve manufacturing efficiency. An entire roll 110 of a blank material is pre-connected or pre-applied with finger grip tapes 30. As discussed above, finger grip tape 30 can be connected using an external adhesive or by heat bonding techniques. The blank material is preferably a paper-based material, such as cardboard, which can be laminated or coated prior to application of finger grip tape 30. In this embodiment, it is preferred that finger grip tapes 30 are applied in approximate parallel pairs (with a space therebetween) across a width of roll 100 and along an entire length of roll 100 (Step 300). Roll 100 is then punched and separated to form each blank 112 so that the pair of pre-applied finger grip tapes 30 are approximately centrally located in parallel relationship to each other and have a space therebetween (Steps 302 and 304). Blank 112 is then convolutely wounded to form a tube 114 (Step 306). Tube 114 is then cut in approximate halves, between the pair of parallel finger grip tapes 30 (i.e., between the space), to form two separate barrels 16 (Steps 308 and 310). An end portion of each barrel 16 is then formed into an insertion tip, preferably having a dome-shape. Such an arrangement provides an efficient and cost effective way of manufacturing an applicator barrel with a finger grip.

The invention having thus been described with particular reference to the preferred forms thereof, it will be obvious that various changes and modifications may be made therein without departing from the spirit and scope of the invention as defined in the appended claims.

What is claimed is:

1. A method of forming a finger grip on a formed applicator barrel, the method comprising the step of:

connecting a three-dimensional tape onto an outer surface of said applicator barrel, said tape having a first surface and a second surface opposite said first surface, said first surface having at least one integrally formed gripping structure on said first surface, said second surface being connected to an adhesive backed label detachably connected to a release liner, prior to connecting said tape to said outer surface of said applicator barrel.

2. The method as recited in claim 1, wherein said tape is affixed to said applicator barrel of an assembled tampon applicator.

3. The method as recited in claim 1, further comprising the step of removing said tape from said release liner, prior to connecting said tape to said outer surface of said applicator barrel.

4. The method as recited in claim 1, wherein said tape comprises a nonwoven material.

5. The method as recited in claim 1, wherein said at least one gripping structure extends outwardly from said first surface.

6. The method as recited in claim 1, wherein said at least one gripping structure extends inwardly from said first surface.

7. The method as recited in claim 1, wherein said three-dimensional tape is embossed to form said at least one gripping structure.

8. The method as recited in claim 1, wherein said three-dimensional tape is debossed to form said at least one gripping structure.

9. A method of forming an applicator barrel with a finger grip, said method comprising the steps of:
connecting a three-dimensional tape to a portion of a first side of a paper-based material blank, said tape including a first surface and a second surface opposite said first surface, said first surface having formed thereon at least one integrally formed gripping structure, said second surface being adhesive to connect said tape onto said first side; and winding said blank to form said applicator barrel in which said first side forms an outer surface of said applicator barrel.

10. The method as recited in claim 9, further comprising the step of forming said blank from paper-based material.

11. The method as recited in claim 9, further comprising the step of securing a second sheet of paper-based material to said blank.

12. The method as recited in claim 9, wherein said blank is convolutely wound.

13. The method are recited in claim 9, wherein said blank is selected from the group consisting of paper laminate and cardboard.

14. The method as recited in claim 9, further comprising the step of applying a coating to said first side of said blank, prior to connecting said tape.

15. The method as recited in claim 14, further comprising the step of curing said coating to form a coated layer to provide insertion comfort and reduced ejection force.

16. The method as recited in claim 15, wherein said coated layer has a coefficient of friction less than a coefficient of friction of said first surface of said tape.

17. The method as recited in claim 9, wherein said connecting step includes the step of heating said second surface of said tape to an elevated temperature so that said second surface becomes adhesive and bonds to said first side of said blank.

18. The method as recited in claim 9, said at least one gripping structure extends outwardly from said first surface.

19. The method as recited in claim 9, wherein said at least one gripping structure extends inwardly from said first surface.

20. The method as recited in claim 9, wherein said three-dimensional tape is embossed to form said at least one gripping structure.

21. The method as recited in claim 9, wherein said three-dimensional tape is debossed to form said at least one gripping structure.

22. A method of forming a finger grip on a formed applicator barrel, the method comprising the step of:
connecting a three-dimensional tape, said tape being formed from synthetic material, onto an outer surface of said applicator barrel, said tape having a first surface and a second surface opposite said first surface, said first surface having at least one embossed gripping structure on said first surface, said second surface being adhesive to connect said tape onto said applicator barrel.

23. The method as recited in claim 22, wherein said tape is affixed to said applicator barrel of an assembled tampon applicator.

24. The method as recited in claim 22, wherein said second surface of said tape is connected to an adhesive backed label detachably connected to a release liner, prior to connecting said tape onto said outer surface of said applicator barrel.

25. The method as recited in claim 24, further comprising the step of removing said tape from said release liner, prior to the connecting step.

26. The method as recited in claim 22, wherein said connecting step includes the step of heating said second surface of said tape to an elevated temperature so that said second surface becomes adhesive and bonds to said outer surface of said barrel.

27. The method as recited in claim 22, wherein said at least one embossed gripping structure extends outwardly from said first surface.

28. A method of forming a finger grip on a formed applicator barrel, the method comprising the step of:
connecting a three-dimensional tape, said tape being formed from synthetic material, onto an outer surface of said applicator barrel, said tape having a first surface and a second surface opposite said first surface, said first surface having at least one debossed gripping structure on said first surface, said second surface being adhesive to connect said tape onto said applicator barrel.

29. The method as recited in claim 28, wherein said tape is affixed to said applicator barrel of an assembled tampon applicator.

30. The method as recited in claim 28, wherein said second surface of said tape is connected to an adhesive backed label detachably connected to a release liner, prior to connecting said tape onto said outer surface of said applicator barrel.

31. The method as recited in claim 30, further comprising the step of removing said tape from said release liner, prior to the connecting step.

32. The method as recited in claim 28, wherein said connecting step includes the step of heating said second surface of said tape to an elevated temperature so that said second surface becomes adhesive and bonds to said outer surface of said barrel.

33. The method as recited in claim 28, wherein said at least one debossed gripping structure extends inwardly from said first surface.

* * * * *